ly W. Fancher, Orinda, Calif.

United States Patent [19]

Fancher

[11] 4,086,239
[45] Apr. 25, 1978

[54] THIAZOLE BIS-PHOSPHATES AND PHOSPHONATES, INTERMEDIATES, AND INSECTICIDAL COMPOSITIONS AND METHODS

[75] Inventor: Llewellyn W. Fancher, Orinda, Calif.

[73] Assignee: Stauffer Chemical Company, Westport, Conn.

[21] Appl. No.: 812,213

[22] Filed: Jul. 1, 1977

[51] Int. Cl.² .................. C07D 277/46; A61K 31/425
[52] U.S. Cl. ............................................. 260/306.8 R
[58] Field of Search .................. 260/306.8 R; 424/200

[56] References Cited

U.S. PATENT DOCUMENTS 3,749,775    7/1973    Fancher .............................. 424/200

*Primary Examiner*—Richard J. Gallagher
*Attorney, Agent, or Firm*—M. Henry Heines

[57] ABSTRACT

Insecticidally active compounds are disclosed, defined by the general formula

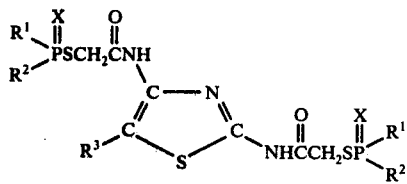

in which
 $R^1$ is methoxy, ethoxy, or alkyl having from 1 to 10 carbon atoms;
 $R^2$ is alkoxy having from 1 to 10 carbon atoms;
 $R^3$ is hydrogen or phenyl; and
 X is sulfur or oxygen;

and intermediates for the preparation of such compounds defined by the general formula

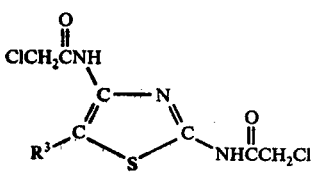

in which $R^3$ is as defined above.

45 Claims, No Drawings

THIAZOLE BIS-PHOSPHATES AND PHOSPHONATES, INTERMEDIATES, AND INSECTICIDAL COMPOSITIONS AND METHODS

BRIEF DESCRIPTION OF THE INVENTION

The present invention relates to a novel class of thiazole bis-phosphates and phosphonates and to their use as insecticides when used in an insecticidally effective amount. In particular, this invention relates to compounds having the formula

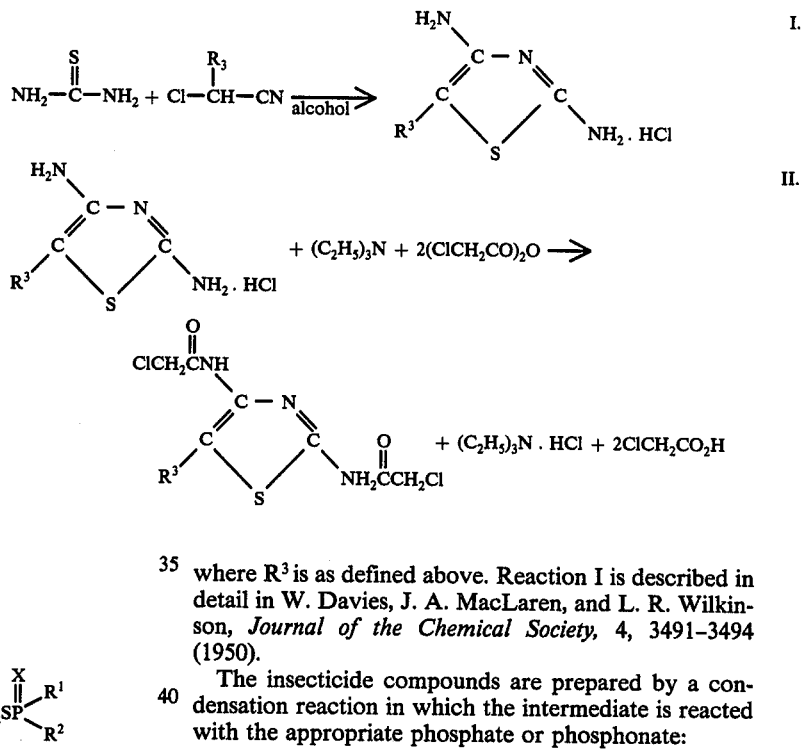

in which
R$^1$ is selected from the group consisting of methoxy, ethoxy, and alkyl having from 1 to 10 carbon atoms, preferably 1 to 5 carbon atoms;
R$^2$ is alkoxy having from 1 to 10 carbon atoms, preferably from 1 to 5 carbon atoms;
R$^3$ is hydrogen or phenyl, preferably hydrogen; and
X is sulfur or oxygen, preferably sulfur.
The present invention further relates to intermediates for the above compounds, having the formula

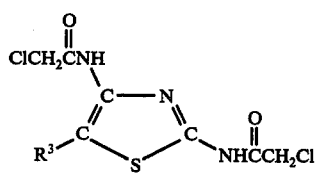

in which R$^3$ is as defined above.

All stated ranges of quantities of carbon atoms are intended to be inclusive of their upper and lower limits.

By "insecticidally effective amount" is meant the amount of the herein disclosed insecticidal compounds which when applied in any conventional manner to the habitat of insects, the feedstuffs of insects, or the insects themselves, will kill or substantially injure a significant portion thereof.

DETAILED DESCRIPTION OF THE INVENTION

The intermediates of the present invention are prepared by the condensation of thiourea with the appropriate α-chloronitrile in alcohol solvent to form the 2,4-diamino-thiazole or the 2,4-diamino-5-phenyl-thiazole, which is subsequently reacted with chloroacetic anhydride in the presence of a base such as triethylamine:

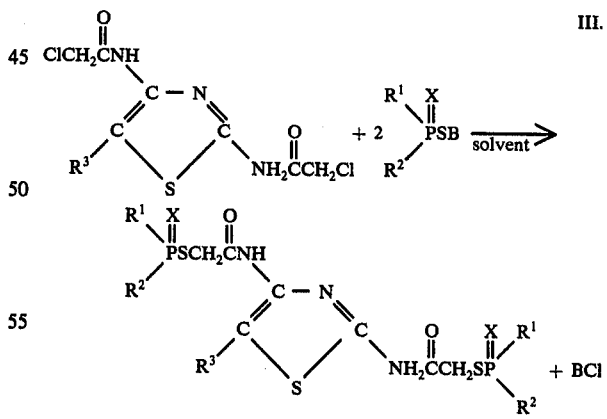

where R$^3$ is as defined above. Reaction I is described in detail in W. Davies, J. A. MacLaren, and L. R. Wilkinson, *Journal of the Chemical Society*, 4, 3491-3494 (1950).

The insecticide compounds are prepared by a condensation reaction in which the intermediate is reacted with the appropriate phosphate or phosphonate:

where R$^1$, R$^2$, and R$^3$ are as defined above, and B is a basic cation such as sodium, potassium, ammonium, or triethylammonium. This reaction can be conducted in the presence of any inert solvent. Due to the low solubility of the intermediate, dimethylformamide or dimethylsulfoxide are preferred solvents.

The following examples are offered to further illustrate the intermediates and insecticide compounds of the present invention.

EXAMPLE 1

2,4-Di-(chloroacetylamino)thiazole

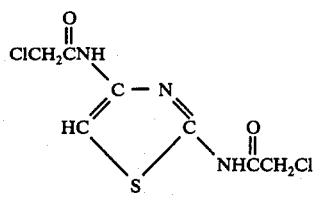

A slurry of 15.2 g (0.1 mole) of 2,4-diaminothiazole prepared according to the method of Davies et al., *J. Chem. Soc.,* 4, 3491-3494 (1950) in 50 ml of dimethylformamide was prepared. To the slurry was added 10.1 g (0.1 mole, 13.8 ml) of triethylamine with continuous stirring, followed by the portion-wise addition of 43 g (0.25 mole) of chloroacetic anhydride with cooling to maintain the temperature at 45° C. The mixture was then warmed to 65°–70° C and filtered. The filtrate was poured over crushed ice and diluted with water. A precipitate formed and was filtered off and washed with cold water followed by ether, then dried at 40° C to produce 18.9 g (70.5% of theory) of the title compounds, melting point 188°–192° C with decompositon.

EXAMPLE 2

2,4-Dichloroacetamido-5-phenylthiazole

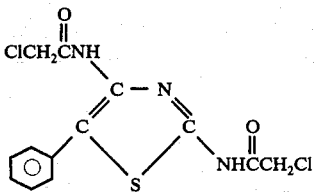

A slurry was prepared, consisting of 11.8 g (0.052 mole) of 2,4-diamino-5-phenylthiazole, prepared according to the method of Davies et al., *J. Chem. Soc.,* 4, 3491-3493 (1950) in 30 ml dimethylformamide. To the stirred mixture was added 25.7 g (0.15 mole) chloroacetic anhydride. The mixture was warmed to 70° C, then cooled in an ice bath. While cooling to beow 40° C, 5.3 g (0.052 mole, 72 ml) of triethylamine were added. The mixture was then heated to 60°–65° C for 5 minutes and filtered. The filtrate was poured into cold water and allowed to stand for 10 minutes, then diluted with ice water. The resulting solid was filtered off, washed consecutively with cold water and ether, and dried at 50° C. The product weighed 6.75 g (37.7% of theory), melting point 215°–216° C. The structure was confirmed by mass spectroscopy as that of the title compound.

EXAMPLE 3

2,4-Bis(O,O-dimethylphosphorodithioylacetamide)thiazole

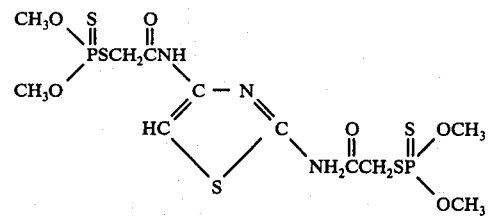

To a continuously stirred solution of 7.0 g (0.04 mole) of ammonium dimethyldithioylphosphate in 25 ml of dimethylformamide was added 4.0 g (0.015 mole) of the compound of Example 1. The mixture was stirred at room temperature for 2.5 hours, allowed to stand overnight, then poured into 150 ml of cold water. To the mixture was then added 50 ml of saturated sodium chloride solution. The resulting mixture was then extracted with benzene and the benzene extract was washed with dilute sodium chloride solution and dried over anhydrous $MgSO_4$, filtered, and vacuum evaporated to give 4.4 g of a thick yellow liquid, with refractive index $n_D^{30}$ = 1.5781. The compound solidified on standing. The structure was confirmed by nuclear magnetic resonance spectra as that of the title compound.

EXAMPLE 4

2,4-Bis-(ethyl, O-isopropylphosphonodithioylacetamido)thiazole

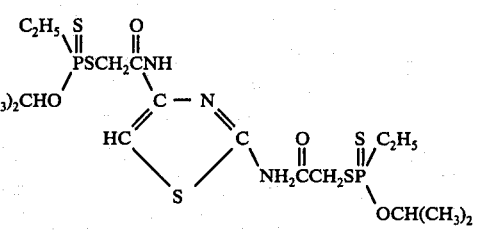

A solution of 9.2 g (0.05 mole, 8.8 ml) of O-isopropyl, ethylphosphonodithioic acid and 5.05 g (0.05 mole) of triethylamine was prepared with stirring and cooling to below 30° C. Additional triethylamine was added to obtain a slightly basic pH. To this mixture was added 5.36 g (0.02 mole) of the compound of Example 1. The mixture was stirred at room temperature and allowed to stand overnight. The mixture was then poured into 150 ml of cold water and 50 ml of saturated sodium chloride were added. The mixture was then extracted with 150 ml of benzene. The benzene extract was washed with dilute sodium chloride solution, dried over anhydrous $MgSO_4$, filtered, and vacuum evaporated to yield 11.4 g of a dark brown liquid product, with refractive index $n_D^{30}$ = 1.5755. The structure was confirmed by nuclear magnetic resonance analysis as that of the title compound.

Other compounds within the scope of the invention can be prepared by similar techniques, using the appropriate starting materials. Further examples are listed in the following tables.

TABLE I
Insecticide Compounds and Physical Properties $$\begin{array}{c} R^1 \\ \diagdown \underset{\parallel}{X} \quad \underset{\parallel}{O} \\ PSCH_2CNHC \\ R^2 \diagup \quad R^3 \diagup C \diagdown\!\!\!\diagup N \\ S \diagup \quad \diagdown C \diagdown \underset{\parallel}{O} \quad \underset{\parallel}{X} \diagup R^1 \\ NHCCH_2SP \\ \diagdown R^2 \end{array}$$

| Compound No. | $R^1$ | $R^2$ | $R^3$ | X | Refractive Index ($n_D^{30}$) |
|---|---|---|---|---|---|
| 1 | $C_2H_5O$ | $C_2H_5O$ | H | S | 1.5754 |
| 2 | $CH_3O$ | $CH_3O$ | H | S | 1.5781 |
| 3 | $C_2H_5$ | $i$-$C_3H_7O$ | H | S | 1.5755 |
| 4 | $C_2H_5$ | $C_2H_5O$ | H | S | 1.5937 |
| 5 | $C_2H_5$ | $CH_3O$ | H | S | 1.6036 |
| 6 | $C_2H_5$ | $i$-$C_4H_9O$ | H | S | 1.5738 |
| 7 | $C_2H_5$ | $s$-$C_4H_9O$ | H | S | 1.5743 |
| 8 | $C_2H_5O$ | $C_2H_5O$ | H | O | 1.5468 |
| 9 | $CH_3O$ | $CH_3O$ | $C_6H_5$ | S | 1.5941 |
| 10 | $C_2H_5$ | $i$-$C_3H_7O$ | $C_6H_5$ | S | dark liquid |

TABLE II
Intermediates and Physical Properties $$\begin{array}{c} O \\ \parallel \\ ClCH_2CNH \\ \diagdown C - N \\ \diagup \quad \diagdown \\ C \quad\quad C \quad O \\ R^3 \diagup \quad \diagdown \quad \diagup \parallel \\ S \quad NHCCH_2Cl \end{array}$$

| Compound No. | $R^3$ | Melting point (° C) |
|---|---|---|
| 11 | H | 194–197 |
| 12 | $C_6H_5$ | 215–216 |

The compounds listed in Table I were evaluated for insecticidal activity according to the following procedures.

Insecticide Evaluation

A. Housefly [*Musca domestica* (L.)]

The test compound is diluted in acetone and an aliquot is pipetted onto the bottom of a 55 × 15 mm aluminum dish. To insure even spreading on the bottom of the dish, 1 ml of acetone containing 0.02% peanut oil is added. After all the solvent has evaporated, the dish is placed in a circular cardboard cage containing 25 1-day-old female houseflies. The cage is covered on the bottom with cellophane and the top with tulle netting, and contains a sugar-water saturated cotton plug for maintenance of the flies. Mortality is recorded after 48 hours. The primary screening level for this test is 100 micrograms of the test compound per 25 female houseflies.

B. German Cockroach [*Blatella germanica* (Linné)]

The test compound is diluted in a 50-50 acetone-water solution. Two milliliters of the solution are sprayed through a DeVilbiss type EGA hand spray gun into a circular cardboard cage contaning 10 1-month-old German Cockroach nymphs. The test cage is covered on the bottom with cellophane and the top with tulle netting. Percent mortality is recorded after 7 days. The primary screening level for this test is 0.1% by weight of the test compound in the acetone-water solution.

C. Lygus bus [*Lygus hesperus* (Knight)]

The test compound is dissolved in a 50-50 acetone-water solution. Two cubic centimeters of the solution are sprayed through a DeVilbiss-type EGA hand spray gun into a circular cardboard cage covered on the bottom with cellophane and the top with tulle netting, containing one string bean pod and 10 adult lygus bugs. Percent mortality is recorded after 48 hours. The primary screening level for this test is 0.5% by weight of the test compound in the acetone-water solution.

D. Direct Spray Assay on Black Bean Aphid [*Aphis fabae* (Scop.)]

A nasturtium plant (Tropaeolum sp.), approximately 5 cm tall, is transplanted into sandy loam soil in a 3-inch clay pot and infested with 25–50 black bean aphids of mixed ages. Twenty-four hours later the plant is sprayed, to the point of runoff, with a 50-50 acetone-water solution of the test chemical. The treated plant is held in the greenhouse and mortality is recorded after 3 days. The primary screening level for this test is 0.05% by weight of the test compound in the acetone-water solution.

E. Direct Spray Assay on Green Peach Aphid [*Myzus persicae* (Sulzer)]

A radish plant (*Rhaphanus sativus*), approximately 2 cm tall, is transplanted into sandy loam soil in a 3-inch clay pot and infested with 25–50 green peach aphids of mixed ages. Twenty-four hours later the plant is sprayed, to the point of runoff, with a 50-50 acetone-water solution of the test compound. The treated plant is held in a greenhouse and mortality is recorded after 3 days. The primary screening level for this test is 0.05% by weight of the test compound in the acetone-water solution.

F. Systemic Assay on Black Bean Aphid [*Aphis fabae* (Scop.)]

The test chemical is diluted in acetone and an aliquot is thoroughly mixed into 500 grams of dry, sandy loam soil. The treated soil is placed in a pint ice cream carton and a nasturtium plant (*Tropaeolum sp.*) approximately 5 cm tall is transplanted into the carton. The plant is then infested with approximately 25 black bean aphids of mixed ages and placed in the greenhouse. Seven days later mortality is recorded. The primary screening level for this test is 10 ppm by weight of the test compound in the soil.

G. Salt-marsh Caterpillar [*Estigmene acrea* (Druryl)]

A test solution is prepared by dissolving the test compound in a 50-50 acetone-water solution. A section of a curly dock (*Rumex crispus*) leaf, aproximately 2.5 centimeters wide and 4 centimeters long, is immersed in the test solution for 2-3 seconds, then placed on a wire screen to dry. The dried leaf is placed in a petri dish containing a moistened piece of filter paper, and infested with 5 second-instar salt-marsh caterpillar larvae. Mortality of the larvae is recorded 48 hours later. If surviving larvae are still present, a piece of synthetic media is added to the dish and the larvae are observed for an additional 5 days in order to detect delayed effects of the test compound. The primary screening level for this test is 0.05% by weight of the test compound in the solution.

H. Cabbage Looper [*Trichoplusia ni* (Hübner)]

The procedure for cabbage looper larvae is the same as that used for salt-marsh caterpillar larvae, except that a cotyledon of hyzini squash (*Calabacita abobrinha*) of approximately the same size as the curly dock leaf section is used in place of the latter. The primary screening level for this test is 0.1% by weight of the test compound in the solution.

I. Tobacco Budworm [*Heliotis virescens* (F.)]

Larvae of the tobacco budworm are used in this test in a procedure identical to that used for salt-marsh caterpillar larvae, except that a Romaine lettuce (*Latua sativa*) leaf section of approximately the same size as the curly dock leaf section is used in place of the latter. The primary screening level for this test is 0.1% by weight of the test compound in the solution.

J. Two-Spotted Mite [*Tetranychus urticae* (Koch)]

A pinto bean plant (*Phaseolus sp.*), approximately 10 cm tall is transplanted into sandy loam soil in a 3-inch clay pot and infested with two-spotted mites of mixed ages and sexes. Twenty-four hours later the infested plants are inverted and dipped for 2-3 seconds in a 50-50 acetone-water solution of the test compound. The treated plant is held in a greenhouse for 7 days. Mortality is then determined for both the adult mites and the nynmphs hatching from eggs which were on the plants at the time of treatment. The primary screening level for this test is 0.05% by weight of the test compound in the acetone-water solution.

K. Southern House Mosquito [*Culex pipiens quinquefasciatus* (Say)]

Insecticidal activity is determined using third-instar larvae of the mosquito (*Culex pipiens quinquefasciatus*). Ten larvae are placed in a 6-ounce, number 67 Dixie wax paper cup containing 100 milliliters of an aqueous solution of the test chemical. The treated larvae are stored at 70° F, and 48 hours later the mortality is recorded. The primary screening level for this test is 1 ppm by weight of the test compound in the solution.

Table III is a summary of the results of tests performed on the compounds of Table I. The entries in Table III were obtained as follows:

For a particular insect, each compound was initially tested at the primary screening level. For the two-spotted mite, the testing stopped at this point. Those compounds showing less than 50% kill are represented in the table by the primary screening level preceded by a "greater than" sign. For those showing more than 50% kill, a "less than" sign is used. For all other insects those compounds showing greater than 50% kill at the primary screening level were then tested at successively lower levels, until the level was found at which approximately 50% kill was achieved. This level is listed as the $LD_{50}$ (50% lethal dose) value in Table III. For those compounds showing approximately 50% kill at the primary screening level, the primary screening level itself is listed as the $LD_{50}$.

Of those compounds which did not pass the primary screen, i.e., those showing less than 50% kill, some were tested at higher concentrations in order to find the level which would produce 50% kill. In cases where this level was found, the level is reported as the $LD_{50}$. When the level of 50% kill was not found, the number listed is the highest concentration tested, whether primary screen or higher, preceded by a "greater than" sign to indicate that a higher level than reported must be used to achieve 50% kill.

The primary screening level in each of the above tests was selected for purposes of convenience only, and none of the figures in the table are to be understood as representing the highest level at which a viable test for insecticidal activity can be conducted. Dashes are used in Table III where no tests were performed at all.

TABLE III

| | Insecticide Activity - Approximate $LD_{50}$ Values | | | | | | | | | | |
|---|---|---|---|---|---|---|---|---|---|---|---|
| | | | | | | | | | | 2SM | |
| Compound No. | HF μg | GR % | LB % | BBA % | GPA % | BAS ppm | SMC % | CL % | TBW % | (1) % | (2) % | MOS ppm |
| 1 | >100 | >.1 | >.05 | .05 | — | >10 | >.05 | >.1 | >.1 | <.05 | <.05 | .8 |
| 2 | >100 | >.1 | >.05 | .002 | .03 | >10 | >.05 | >.1 | >.1 | <.05 | >.05 | >1.0 |
| 3 | 100 | >.1 | .05 | .00005 | .001 | >10 | .008 | .002 | .005 | <.05 | <.05 | .1 |
| 4 | 100 | >.1 | .05 | .0003 | .002 | >10 | .01 | .005 | .05 | <.05 | <.05 | .08 |
| 5 | 75 | >.1 | >.05 | .0005 | .005 | >10 | .05 | .02 | >.05 | <.05 | <.05 | .2 |
| 6 | 42 | >.1 | >.05 | .0001 | .005 | >10 | .005 | .003 | .05 | <.05 | <.05 | .08 |
| 7 | >100 | >.1 | >.05 | .0001 | .005 | >10 | .01 | .002 | >.1 | <.05 | <.05 | .2 |
| 8 | >100 | >.1 | >.05 | .001 | .03 | >10 | >.05 | >.1 | >.1 | <.05 | <.05 | >1.0 |
| 9 | >100 | — | — | .2 | .15 | — | >.05 | >.5 | — | >.05 | <.05 | >1.0 |
| 10 | >100 | >.1 | >.05 | .0002 | .005 | >10 | >.05 | >.1 | >.1 | <.05 | <.05 | .4 |

Symbols for Table III:
HF : housefly
GR : German cockroach
LB : Lygus bug
BBA : black bean aphid
GPA : green peach aphid
BAS : bean aphid systemic
SMC : salt-marsh caterpillar
CL : cabbage looper
TBW : tobacco budworm
2SM : two-spotted mite - (1) post-embryonic, (2) eggs
MOS : Southern house mosquito
\> : greater than
< : less than The compounds of this invention are generally used in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents, talc; pyrophyllite; diatomite; diatomite; gypsum; clays; and propellants, such as dichlorodifluoromethane.

The active compounds can further be combined with dust carriers for application as dusts, with granular carriers for application by fertilizer spreaders or ground or airplane seeders, with wettable powders or flowable carriers for application as water suspensions, or with solvents and surface active materials for application as sprays, aerosols, or emulsions. The compounds or their formulated mixtures can be applied to any habitat of the pests. Examples of such habitats are insect dwellings, clothing, plant surfaces, and soil. If desired, however, the active compositions can be applied directly to organic matter, seeds or feedstuffs in general, upon which the pests feed, or directly to the pests themselves. When applied in such a manner, it will be advantageous to use a formulation which is not volatile.

The amount of active compound or formulation which is considered to be insecticidally effective is that amount which, when applied to the pest habitat or feedstuff, will kill or substantially injure a significant portion residing or feeding thereon. The active compounds of this invention can be employed either as the sole pesticide component of the formulation or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, odinarily, the pesticide composition will comprise not more than about 50.0% by weight of the formulation.

What is claimed is:

1. A compound having the formula $$\begin{array}{c} R^1 \\ \diagdown \\ R^2 \end{array} \overset{X}{\underset{\|}{P}} SCH_2 \overset{O}{\underset{\|}{C}} NH \diagdown \\ \phantom{xxxxx} C \text{---} N \\ R^3 \overset{\|}{\underset{C}{\diagdown}} \diagup \overset{C}{\underset{S}{\diagup}} \diagdown \underset{NHCCH_2SP}{\overset{O}{\underset{\|}{}}} \overset{X}{\underset{\|}{}} R^1 \\ \phantom{xxxxxxxxxxxxxxxxxxxx} R^2 \end{array}$$

in which $R^1$ is selected from the group consisting of methoxy, ethoxy, and alkyl having from 1 to 10 carbon atoms; $R^2$ is alkoxy having from 1 to 10 carbon atoms; $R^3$ is hydrogen or phenyl; and X is oxygen or sulfur.

2. A compound according to claim 1 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is oxygen or sulfur.

3. A compound according to claim 1 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is sulfur.

4. A compound according to claim 1 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen; and X is sulfur.

5. A compound according to claim 1 in which $R^1$ is $C_2H_5O$, $R^2$ is $C_2H_5O$, $R^3$ is hydrogen and X is sulfur.

6. A compound according to claim 1 in which $R^1$ is $CH_3O$, $R^2$ is $CH_3O$, $R^3$ is hydrogen and X is sulfur.

7. A compound according to claim 1 in which $R^1$ is $C_2H_5$, $R^2$ is i-$C_3H_7O$, $R^3$ is hydrogen and X is sulfur.

8. A compound according to claim 1 in which $R^1$ is $C_2H_5$, $R^2$ is $C_2H_5O$, $R^3$ is hydrogen and X is sulfur.

9. A compound according to claim 1 in which $R^1$ is $C_2H_5$, $R^2$ is $CH_3O$, $R^3$ is hydrogen and X is sulfur.

10. A compound according to claim 1 in which $R^1$ is $C_2H_5$, $R^2$ is i-$C_4H_9O$, $R^3$ is hydrogen and X is sulfur.

11. A compound according to claim 1 in which $R^1$ is $C_2H_5$, $R^2$ is s-$C_4H_9O$, $R^3$ is hydrogen and X is sulfur.

12. A compound according to claim 1 in which $R^1$ is $C_2H_5O$, $R^2$ is $C_2H_5O$, $R^3$ is hydrogen and X is oxygen.

13. A compound according to claim 1 in which $R^1$ is $CH_3O$, $R^2$ is $CH_3O$, $R^3$ is $C_6H_5$ and X is sulfur.

14. A compound according to claim 1 in which $R^1$ is $C_2H_5$, $R^2$ is i-$C_3H_7O$, $R^3$ is $C_6H_5$ and X is sulfur.

15. A compound having the formula $$\begin{array}{c} \overset{O}{\underset{\|}{}} \\ ClCH_2CNH \diagdown \\ \phantom{xxxx} C\text{---}N \\ R \overset{\|}{\underset{C}{\diagdown}} \diagup \overset{C}{\underset{S}{\diagup}} \diagdown \underset{NHCCH_2Cl}{\overset{O}{\underset{\|}{}}} \end{array}$$

in which R is hydrogen or phenyl.

16. A compound according to claim 15 in which R is hydrogen.

17. A compound according to claim 15 in which R is phenyl.

18. An insecticidally effective composition of matter comprising 1. an insecticidally effective amount of a compound having the formula $$\begin{array}{c} R^1 \\ \diagdown \\ R^2 \end{array} \overset{X}{\underset{\|}{P}} SCH_2 \overset{O}{\underset{\|}{C}} NH \diagdown \\ \phantom{xxxxx} C\text{---}N \\ R^3 \overset{\|}{\underset{C}{\diagdown}} \diagup \overset{C}{\underset{S}{\diagup}} \diagdown \underset{NHCCH_2SP}{\overset{O}{\underset{\|}{}}} \overset{X}{\underset{\|}{}} R^1 \\ \phantom{xxxxxxxxxxxxxxxxxxxx} R^2 \end{array}$$

in which $R^1$ is selected from the group consisting of methoxy, ethoxy, and alkyl having from 1 to 10 carbon atoms; $R^2$ is alkoxy having from 1 to 10 carbon atoms; $R^3$ is hydrogen or phenyl; and X is oxygen or sulfur; and 2. an inert diluent carrier.

19. A composition according to claim 18 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is oxygen or sulfur.

20. A composition according to claim 18 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is sulfur.

21. A composition according to claim 18 in whiwh $R^1$ is selected from the group consisting of methoxy, ethoxy, and alkyl having from 1 to 5 carbon atoms; $R^2$ is alkoxy having from 1 to 5 carbon atoms; $R^3$ is hydrogen; and X is sulfur.

22. A composition according to claim 18 in which $R^1$ is $C_2H_5O$, $R^2$ is $C_2H_5O$, $R^3$ is hydrogen and X is sulfur.

23. A composition according to claim 18 in which $R^1$ is $CH_3O$, $R^2$ is $CH_3O$, $R^3$ is hydrogen and X is sulfur.

24. A composition according to claim 18 in which $R^1$ is $C_2H_5$, $R^2$ is i-$C_3H_7O$, $R^3$ is hydrogen and X is sulfur.

25. A composition according to claim 18 in which $R^1$ is $C_2H_5$, $R^2$ is $C_2H_5O$, $R^3$ is hydrogen and X is sulfur.

26. A composition according to claim 18 in which $R^1$ is $C_2H_5$, $R^2$ is $CH_3O$, $R^3$ is hydrogen and X is sulfur.

27. A composition according to claim 18 in which $R^1$ is $C_2H_5$, $R^2$ is i-$C_4H_9O$, $R^3$ is hydrogen and X is sulfur.

28. A composition according to claim 18 in which $R^1$ is $C_2H_5$, $R^2$ is s-$C_4H_9O$, $R^3$ is hydrogen and X is sulfur.

29. A composition according to claim 18 in which $R^1$ is $C_2H_5O$, $R^2$ is $C_2H_5O$, $R^3$ is hydrogen and X is oxygen.

30. A composition according to claim 18 in which $R^1$ is $CH_3O$, $R^2$ is $CH_3O$, $R^3$ is $C_6H_5$, and X is sulfur.

31. A composition according to claim 18 in which $R^1$ is $C_2H_5$, $R^2$ is i-$C_3H_7O$, $R^3$ is $C_6H_5$ and X is sulfur.

32. A method of controlling insects comprising applying to said insects or to the habitat or feedstuffs of said insects an insecticidally effective amount of a compound having the formula

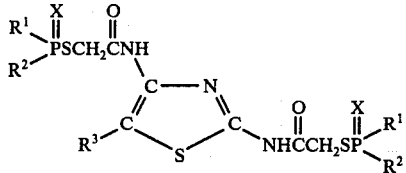

in which $R^1$ is selected from the group consisting of methoxy, ethoxy, and alkyl having from 1 to 10 carbon atoms; $R^2$ is alkoxy having from 1 to 10 carbon atoms; $R^3$ is hydrogen or phenyl; and X is oxygen or sulfur.

33. A method according to claim 32 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is oxygen or sulfur.

34. A method according to claim 32 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen or phenyl; and X is sulfur.

35. A method according to claim 32 in which $R^1$ is selected from the group consisting of methoxy, ethoxy, and alkyl having from 1 to 5 carbon atoms; $R^2$ is alkoxy having from 1 to 5 carbon atoms; $R^3$ is hydrogen; and X is sulfur.

36. A method according to claim 32 in which $R^1$ is $C_2H_5O$, $R^2$ is $C_2H_5O$, $R^3$ is hydrogen and X is sulfur.

37. A method according to claim 32 in which $R^1$ is $CH_3O$, $R^2$ is $CH_3O$, $R^3$ is hydrogen and X is sulfur.

38. A method according to claim 32 in which $R^1$ is $C_2H_5$, $R^2$ is i-$C_3H_7O$, $R^3$ is hydrogen and X is sulfur.

39. A method according to claim 32 in which $R^1$ is $C_2H_5$, $R^2$ is $C_2H_5O$, $R^3$ is hydrogen and X is sulfur.

40. A method according to claim 32 in which $R^1$ is $C_2H_5$, $R^3$ is $CH_3O$, $R^4$ is hydrogen and X is sulfur.

41. A method according to claim 32 in which $R^1$ is $C_2H_5$, $R^2$ is i-$C_4H_9O$, $R^3$ is hydrogen and X is sulfur.

42. A method according to claim 32 in which $R^1$ is $C_2H_5$, $R^2$ is s-$C_4H_9O$, $R^3$ is hydrogen and X is sulfur.

43. A method according to claim 32 in which $R^1$ is $C_2H_5O$, $R^2$ is $C_2H_5O$, $R^3$ is hydrogen and X is oxygen.

44. A method according to claim 32 in which $R^1$ is $CH_3O$, $R^2$ is $CH_3O$, $R^3$ is $C_6H_5$, and X is sulfur.

45. A method according to claim 32 in which $R^1$ is $C_2H_5$, $R^2$ is i-$C_3H_7O$, $R^3$ is $C_6H_5$ and X is sulfur.

* * * * *